United States Patent
Bosy et al.

(10) Patent No.: US 11,231,409 B2
(45) Date of Patent: Jan. 25, 2022

(54) DISPOSABLE HEMOLYSIS SENSOR

(71) Applicant: Instrumentation Laboratory Company, Bedford, MA (US)

(72) Inventors: Brian Joseph Bosy, Hull, MA (US); Josef Kerimo, Concord, MA (US)

(73) Assignee: INSTRUMENTATION LABORATORY COMPANY, Bedford, MA (US)

( * ) Notice: Subject to any disclaimer, the term of this patent is extended or adjusted under 35 U.S.C. 154(b) by 74 days.

(21) Appl. No.: 16/591,413

(22) Filed: Oct. 2, 2019

(65) Prior Publication Data

US 2020/0103395 A1 Apr. 2, 2020

Related U.S. Application Data

(60) Provisional application No. 62/740,117, filed on Oct. 2, 2018.

(51) Int. Cl.
*G01N 33/49* (2006.01)
*G01N 15/14* (2006.01)

(52) U.S. Cl.
CPC ..... *G01N 33/4915* (2013.01); *G01N 15/1404* (2013.01); *G01N 33/491* (2013.01); *G01N 2015/142* (2013.01)

(58) Field of Classification Search
CPC ......... G01N 15/1404; G01N 2015/142; G01N 2021/3181; G01N 21/3151; G01N 33/491; G01N 33/4915; G01N 33/49; G01N 33/721
USPC .......................................................... 356/40
See application file for complete search history.

(56) References Cited

U.S. PATENT DOCUMENTS

| 4,854,170 | A | 8/1989 | Brimhall et al. |
| 5,902,489 | A | 5/1999 | Yasuda et al. |
| 5,992,489 | A | 5/1999 | Yasuda et al. |
| 7,003,153 | B1 * | 2/2006 | Kerofsky ................ G06T 5/009 |
| | | | 348/E5.119 |
| 7,484,414 | B2 | 2/2009 | Priev et al. |
| 8,846,408 | B2 | 9/2014 | Ward et al. |
| 8,885,003 | B2 | 10/2014 | Yang |
| 9,494,570 | B2 * | 11/2016 | Bransky ............ G01N 15/1484 |

(Continued)

FOREIGN PATENT DOCUMENTS

| AU | 2016208974 B2 | 10/2018 |
| CN | 102257413 A | 11/2011 |

(Continued)

OTHER PUBLICATIONS

International Preliminary Report on Patentability for International Patent Application No. PCT/US2019/054289, dated Apr. 15, 2021, 8 pages.

(Continued)

*Primary Examiner* — Sunghee Y Gray
(74) *Attorney, Agent, or Firm* — Burris & Levinson LLP

(57) ABSTRACT

An apparatus for measuring hemolysis in a cartridge based automated blood analyzer is described. The apparatus allows hemolysis testing to be performed on a sample which is presented as a whole blood sample for other testing by the cartridge based automated blood analyzer. A disposable module is configured for optically analyzing one or more plasma analytes in a flow cell while red blood cells are acoustically separated from plasma in the flow cell.

20 Claims, 4 Drawing Sheets

(56) References Cited

U.S. PATENT DOCUMENTS

| | | | |
|---|---|---|---|
| 9,656,265 | B2 | 5/2017 | Adolfsen et al. |
| 2005/0106064 | A1 | 5/2005 | Laurell et al. |
| 2012/0214224 | A1 | 8/2012 | Chan |
| 2013/0043170 | A1 | 2/2013 | Rose et al. |
| 2013/0104369 | A1* | 5/2013 | Alferness .......... A61B 5/150358 29/428 |
| 2013/0156644 | A1 | 6/2013 | Lee et al. |
| 2014/0273858 | A1* | 9/2014 | Panther ............... A61B 5/02427 455/41.2 |
| 2014/0305196 | A1* | 10/2014 | Ellis ................. A61B 5/150022 73/64.56 |
| 2014/0336062 | A1 | 11/2014 | Graves et al. |
| 2015/0253226 | A1 | 9/2015 | Augustsson et al. |
| 2015/0308971 | A1 | 10/2015 | Bisgaard et al. |
| 2016/0202237 | A1 | 7/2016 | Zeng et al. |
| 2017/0010210 | A1* | 1/2017 | Choung ................. G01N 33/02 |
| 2018/0049686 | A1* | 2/2018 | Marchiarullo ... A61B 5/150267 |
| 2018/0052147 | A1 | 2/2018 | Zeng |
| 2018/0106720 | A1* | 4/2018 | Schonbrun ............. G01N 21/27 |

FOREIGN PATENT DOCUMENTS

| | | | |
|---|---|---|---|
| DE | 102004013960 | A1 | 8/2005 |
| EP | 0795129 | A1 | 9/1997 |
| EP | 3245001 | A1 | 4/2021 |
| JP | 2001/258868 | | 9/2001 |
| JP | 2008/051824 | | 3/2008 |
| WO | 2005/089082 | | 9/2005 |
| WO | 2010038230 | A1 | 4/2010 |
| WO | 2011006525 | A1 | 1/2011 |
| WO | 2013177580 | A1 | 11/2013 |
| WO | 2014178782 | A1 | 11/2014 |
| WO | 2018/065626 | | 4/2018 |
| WO | 2018065626 | A1 | 4/2018 |

OTHER PUBLICATIONS

Christopher-John L Farrell et al.: "Serum indices: managing assay interference", Annals of Clinical Biochemistry., vol. 53, No. 5, Sep. 1, 2016, pp. 527-538, XP055652917, GB ISSN: 0004-5632, DOI: 10.1177/0004563216643557.
Farkas et al. Thermochimica Acta, 2003, 404, pp. 141-148.
Henkelman et al. Materials Science and Engineering C 29 (2009) 1650-1654.
Jonsson et al. Ann Thorac Surg 2004, 78: 1572-1577.
Lenshof et al. "Acoustic Whole Blood Plasmapheresis Chip for Prostate Specific Antigen Microarray Diagnostic". Anal. Chem. 2009, 81, 6030-6037.
Final Office Action for U.S. Appl. No. 14/992,284, dated Jul. 16, 2021, (18 pages).
Final Office Action for U.S. Appl. No. 15/791,734, dated Dec. 28, 2020, (24 pages).
Non-Final Office Action for U.S. Appl. No. 15/791,734, dated Jun. 9, 2021, (25 pages).
Non-Final Office Action for U.S. Appl. No. 14/992,284, dated Feb. 23, 2021, (12 pages).
Elodie Sollier et al. Micro-scale blood plasma separation: from acoustophoresis to egg-beaters, Lab on a Chip, 2013,13, Issue 17, 1-24; doi: 10.1039/c3lc50432h.
Gossett et al. Label-free cell separation and sorting in microfluidic systems, Anal Bioanal Chem (2010) 397:3249-3267, DOI 10.1007/s90216-010-3721-9.
Chwee Teck Lim et ai. Microfluidic Devices for Blood Fractionation, Micromachines 2011,2, 319-343; doi:10.3390/m12030319.
Tao Dong et al. Review: Recent Developments in Optical Detection Technologies in Lab-on-a-Chip Devices for Biosensing Applications, Sensors, 2014, 14, 15458-15479; doi:10.3390/s140815458.
Hun Lee et al. Review: Various On-Chip Sensors with Microfluidics for Biological Applications. Sensors 2014, 14, 17008-17036; doi: 10.3390/s149917006.
Examiner Requisition for Canadian patent application No. 2,972,848, dated Apr. 19, 2021, (9 pages).
Third Office Action for Chinese patent application No. 2016800056038, dated Oct. 30, 2020, with English translation, (14 pages).
Examination Report issued in corresponding Canadian application No. 2,972,848, dated Oct. 14, 2019, 5 pages.
Chinese Office Action issued in corresponding Chinese application No. 2016800056038, dated Jul. 8, 2019, and English translation thereof, 12 pages.
Communication pursuant to Article 94(3) EPC issued in European Patent Application No. 16 703 385.1, dated Jun. 25, 2019, 5 pages.
Australian Examination Report issued in Australian Patent Application No. 2018236886, dated Jul. 8, 2019, 3 pages.
Canadian Office Action for Canadian Patent Application No. 2,972,848 dated Oct. 22, 2018, 4 pages.
Manneberg, "Flow-free Transport of Ceils in Microchannels by Frequency-modulated Ultrasound", The Royal Society of Chemistry, 2009, vol. 9, pp. 833-837.
Final Rejection dated Sep. 5, 2018 in U.S. Publication No. 2018/0052147, 14 pages.
Japanese Office Action, Application No. 2017-534914, dated Jul. 9, 2018, 9 pages (includes both English and Japanese language versions).
Non-Final Rejection dated Feb. 15,2018 in the U.S. Pub. No. 20180052147; 9 pgs.
International Preliminary Report on Patentability, dated Jul. 18, 2017, International Application No. PCT/US2016/012811, pp. 1-6.
International Search Report and Written Opinion for International Application No. PCT/US2016/012811, dated Apr. 15, 2016, 11 pages.
De Sarabia et al., "Application of high-power ultrasound to enhance fluid/solid particle separation processes," *Ultrasonics*, 38:642-646 (2000).
Jönsson et al., "Particle Separation Using Ultrasound Can Radically Reduce Embolic Load to Brain After Cardiac Surgery," *Ann Thorac Surg.*, 78:1572-1577 (2004).
Adams et al., "High-throughput, temperature-controlled microchannel acoustophoresis device made with rapid prototyping," *J. Micromech. Microeng.*, 22:1-8 (2012).
Chen et al., "Standing surface acoustic wave (SSAW)-based microfluidic cytometer," *Lab Chip*, 14:916-923 (2014).
Laurell, "Chip integrated strategies for acoustic separation and manipulation of cells and particles," *Chem. Soc. Rev.*, 36:493-506 (2007).
Petersson, et al., "Separation of lipids from blood utilizing ultrasonic standing waves in microfluidic channels," *Analyst*, 129:938-943 (2004).

\* cited by examiner

DISPOSABLE HEMOLYSIS SENSOR

CROSS REFERENCE TO RELATED APPLICATIONS

This application claims priority to U.S. Provisional Patent Application No. 62/740,117 entitled Disposable Hemolysis Sensor which was filed on Oct. 2, 2018 and which is incorporated by reference herein in its entirety.

BACKGROUND

Automated blood analyzers, which are commonly used for efficiently testing numerous properties of a blood sample, generally accept disposable test cartridges. The disposable cartridges may include blood sample pathways, sensor devices, storage packages for storing appropriate reagents, chambers and fluid pathways for presenting the appropriate reagents and mixtures to a blood sample for testing. An example of an automated blood analyzer is the GEM Premier 5000 system manufactured by Instrumentation Laboratories of Bedford, Mass., USA. The GEM premier 5000 system provides fast, accurate, quantitative measurements of whole blood pH, $pCO_2$, $pO_2$, $Na^+$, $K^+$, $Cl^-$, $Ca^{++}$, glucose, lactate, haematocrit, total bilirubin and CO-Oximetry (tHb, O2Hb, COHb, MetHb, HHb).

Clinical utility of each measurement described is well known. For example, pH and $pCO_2$, along with their derived parameters Base Excess, standard bicarbonate, and $TCO_2$, define acid-base status. Arterial $pO_2$ indicates adequacy of oxygen exchange. Electrolytes in the human body have multiple roles. Nearly all metabolic processes depend on or vary with electrolytes. Haematocrit (Hct) indicates the red cell fraction of the blood, a vital component in determining its oxygen carrying capacity. Glucose (Glu) is the primary energy source, and its blood level is maintained within a fairly narrow range. Lactate (Lac) is an intermediary product of carbohydrate metabolism and is derived mainly from muscle cells and erythrocytes. Bilirubin (tBili) is produced by the degradation of heme groups present in haemoglobin. CO-Oximetry (tHb, COHb, MetHb, $O_2$Hb and HHb) evaluates the ability of the blood to carry oxygen by measuring total haemoglobin and determining the percentage of functional and dysfunctional haemoglobin species. Carboxyhaemoglobin is a stable complex of carbon monoxide and haemoglobin. Haemoglobin binds to carbon monoxide preferentially compared to oxygen and has a strong affinity that the carbon monoxide is not released therefore reducing the oxygen carrying capacity in the body. Methaemoglobin is a form of the oxygen-carrying metalloprotein haemoglobin in which the iron in the heme group is in the ferric ($Fe^{3+}$) state and not the ferrous ($Fe^{2+}$) of normal haemoglobin. It is usual to have 1-2% of methaemoglobin in normal circulation; the NADH-dependent enzyme methaemoglobin reductase is responsible for converting methaemoglobin back to haemoglobin It would be desirable to also measure hemolysis in a cartridge based automated blood analyzer. However, hemolysis has historically been measured by analyzing blood plasma which has been separated from a whole blood sample by centrifugation, for example. It would be desirable to perform hemolysis testing on a sample which is presented as a whole blood sample for other testing by the cartridge based automated blood analyzer.

SUMMARY

Aspects of the present disclosure include a disposable hemolysis sensor that can be used inside a cartridge of a blood analysis instrument to measure the level of hemolysis in whole blood. In an illustrative embodiment, the disclosed hemolysis sensor is a self-contained module that contains only disposable components. The self-contained module can be installed in-line inside an existing instrument cartridge such as a GEM instrument cartridge made by Instrumentation Laboratories of Bedford, Mass., USA. The disclosed module may be installed between an EC card and a COOx card of the GEM Premier 5000 system, for example.

In an illustrative embodiment, operation of the disclosed sensor employs acoustic separation of whole blood into blood cells and plasma within a flow cell. The disposable hemolysis sensor includes, the flow cell, an acoustic transducer, a multicolor light emitting diode [LED] illumination source, and a camera. The camera may be a low-cost camera configured to acquire images of the plasma while separated from the blood cells. The images are later processed to obtain a plasma hemoglobin level. According to an aspect of the present disclosure, the disposable sensor includes a housing such as a two-piece split housing, for example, that is configured to locate the camera, LED illumination source, and flow cell in a fixed alignment and orientation relative to each other. The housing is also configured such that the module can be removably installed in the instrument cartridge.

The present application describes the design of the disposable sensor apparatus and the process of performing a reliable measurement of plasma hemoglobin using the disclosed sensor apparatus.

Aspects of the present disclosure include a disposable module for measuring free hemoglobin in plasma. The disposable module contains light source, piezo transducer, flow cell, optical imaging sensor, and optical elements (lenses, filters, diffuser, and mixing light pipe). In an illustrative embodiment, the sensor module that consist of a split housing which includes slots for positioning flow cell, light source, imaging sensor, and optical elements. The split housing is configured to keep the flow cell in a tight alignment tolerance relative to imaging sensor. Another aspect of the present disclosure includes an optical design for correcting variations in the illumination pattern of different colors using a light pipe. Another aspect of the present disclosure includes a diffuser element for uniformly illuminating the flow cell. Another aspect of the present disclosure includes an optical aperture installed at the imaging lenses for controlling optical aberrations. Another aspect of the present disclosure includes a single connector configured to pass powers and control signals to and from the sensor module.

A method for processing image data and outputting a free hemoglobin concentration such as a histogram of OD or concentration images is described according to an aspect of the present disclosure. According to another aspect of the present disclosure a method is disclosed for correcting variations in the intensity of the light source. Wavelength selection for the illumination source for effective correction of interferences such as bilirubin and lipid present in plasma is described according to another aspect of the present disclosure. A process for calculating extinction coefficient when a broadband light source is used.

DETAILED DESCRIPTION

Figure 1:
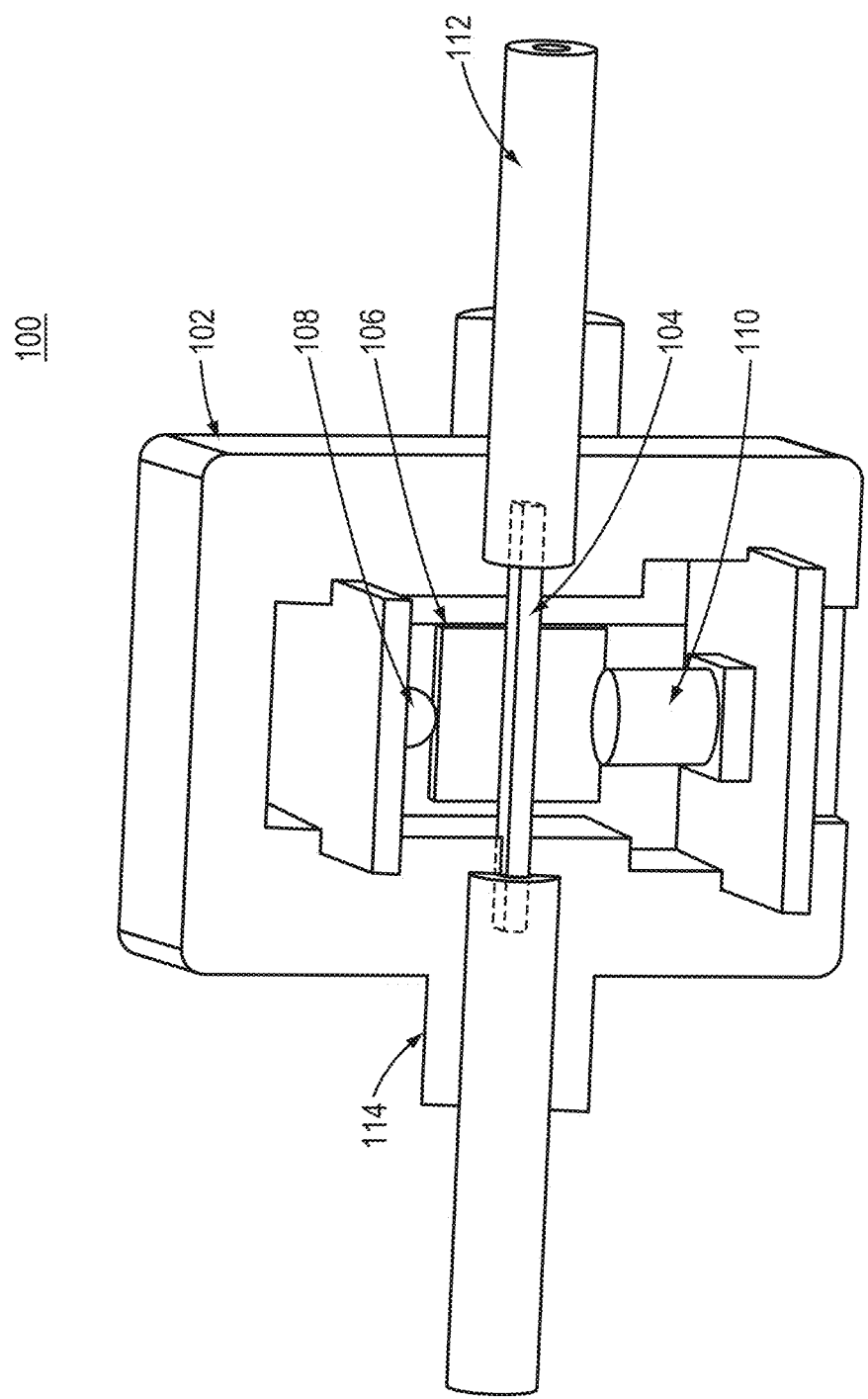
FIG. 1 shows a high level diagram of the construction of the hemolysis sensor.

An illustrative embodiment of a hemolysis sensor according to an aspect of the present disclosure is described with reference to FIG. 1. The hemolysis sensor 100 includes a housing 102, which secures a transparent flow cell 104, such as a glass capillary tube, in a fixed position relative to the housing 102. FIG. 1 is a cut-away view of a hemolysis sensor 100 in which only a back portion of the housing 102 is shown.

An acoustic transducer 106 such as a piezo electric transducer is arranged in the housing in proximity to the flow cell 104 such that acoustic forces can be applied by the acoustic transducer 106 to the flow cell 104 while a column of blood flows through the flow cell 104 or is contained in the flow cell 104. According to an aspect of the present disclosure, the acoustic transducer 106 is responsive to an electrical signal to generate acoustic forces that cause separation of red blood cells from plasma in the column of blood.

A light source 108 is secured by the housing in a fixed position relative to the flow cell. The light source 108 is arranged to transmit light waves through the flow cell 104 to a blood sample that is flowing through or contained in the flow cell 104 while the flow cell is subjected to the acoustic forces. More particularly, the light source is arranged to transmit the light waves through a plasma portion of the blood sample that is separated from red blood cells in the flow cell. In an illustrative embodiment, the light source 108 includes a multi-color light emitting diode, for example.

An optical sensor 110 such as a camera is secured by the housing in a fixed position relative to the flow cell 104 and the light source 108. The optical sensor may include an image board, imaging lenses and an aperture, for example. The optical sensor 110 is arranged to receive light waves from the light source after the light waves have interacted with the plasma portion of the blood sample in the flow cell 104.

The housing 102 includes an inlet port 112 and an outlet port 114 that are configured such that the hemolysis sensor 100 can be installed in-line with a blood column of a blood sample flowing within an automated blood analysis instrument. In the illustrative embodiment, the inlet port 112 and outlet port 114 are configured for coupling of a rubber tubing portion of a sample flow path in the automated blood analysis instrument to and from the flow cell 104.

According to an illustrative embodiment, the hemolysis sensor 100 also includes an electrical connector (not shown) configured to deliver power and control signals to the acoustic transducer 106 and the light source 108 and to receive signals from the optical sensor 110.

According to an aspect of the present disclosure, the hemolysis sensor 100 is disposable to provide an inline sensor that can be retrofitted into an existing instruments, and to provide tight dimensional tolerances for proper alignment of the glass flow cell relative to the imaging camera. This prevents or reduces misalignments and recalibrations, for example. Packaging of all the components into a self-contained sensor module provides a robust and reliable hemolysis sensor that is easy to retrofit into an existing instrument.

Figure 2:
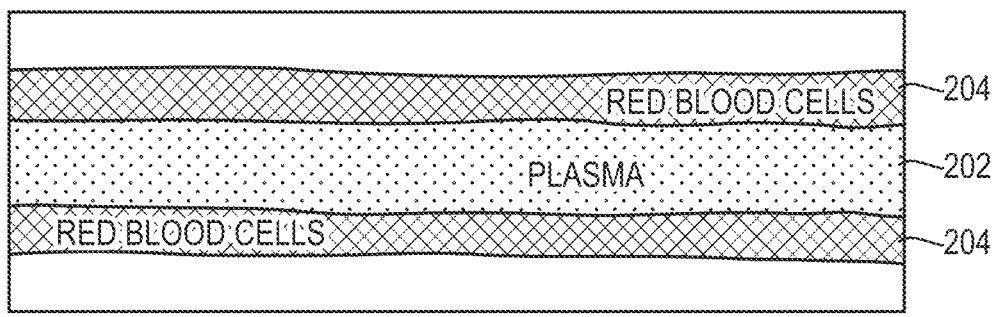
FIG. 2. An example of an image of separated blood plasma acquired with an embodiment of the disclosed sensor module.

An example of an image 200 acquired with the disclosed hemolysis sensor module is shown in FIG. 2. This figure shows an image of a blood sample inside of a flow cell 104 in which plasma 202 has been separated from red blood cells 204 by forces applied to the flow cell 104 by the acoustic transducer 106. This acoustic separation allows clear plasma to be interrogated optically in the flow cell 104 to determine a free hemoglobin level of the blood sample. In the illustrative embodiment, the image 200 was acquired by illuminating the plasma with a multicolored LED source packaged inside the sensor module.

According to an aspect of the present disclosure it has been determined that two LED colors are sufficient to measure free hemoglobin in the plasma and to avoid difficulties with possible interferences in the plasma. The preferred colors are yellow and red corresponding to wavelengths of about 570 nanometers and about 610 nanometers. According to an aspect of the present disclosure, these colors avoid or reduce effects of interferences on the hemoglobin measurement.

Figure 3:
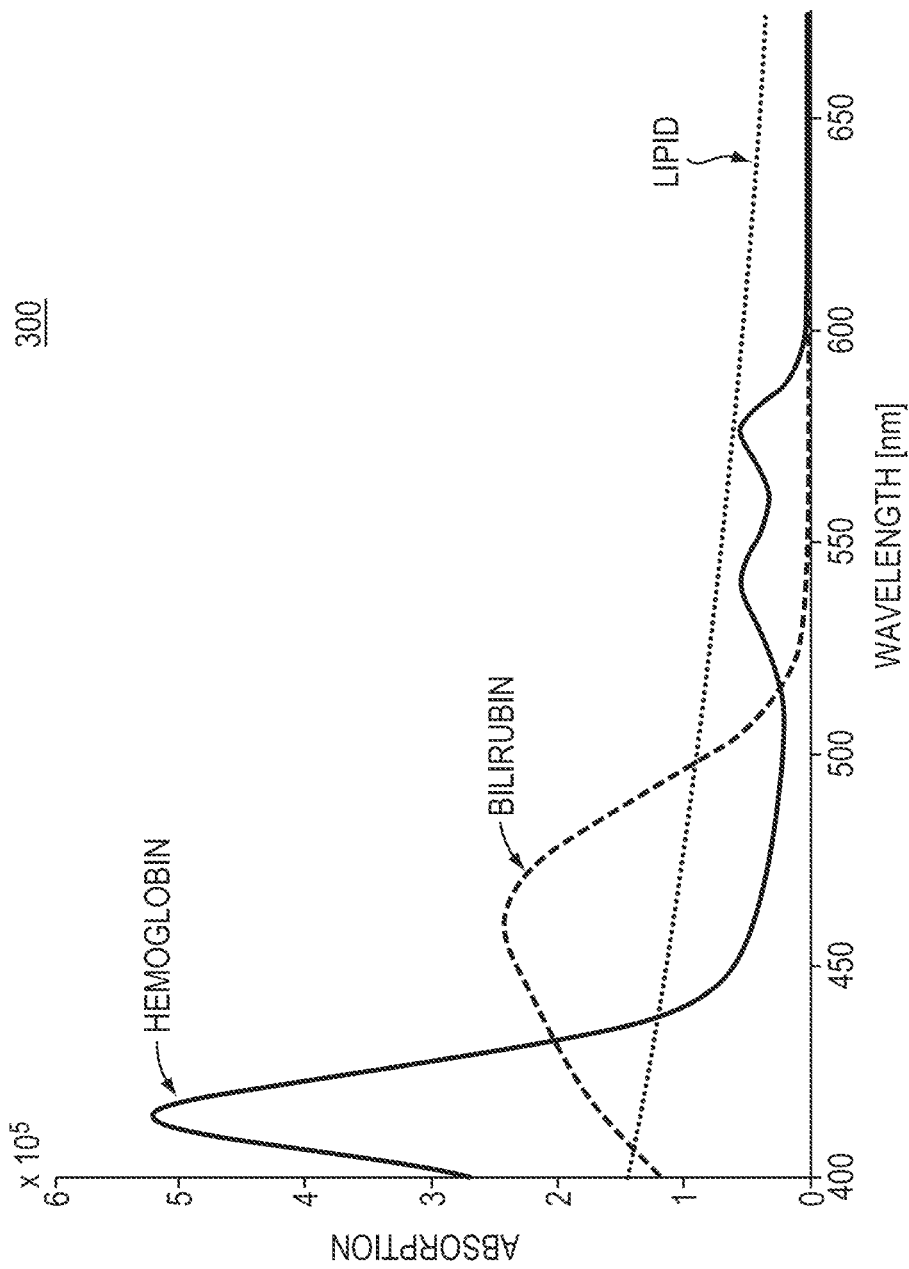
FIG. 3 is a graph 300 showing the absorption spectra of hemoglobin, bilirubin, lipid.

The effects of the interferences can be seen on the absorption spectra of hemoglobin and of the most common interferences present in plasma, i.e., bilirubin interference and lipid interference. FIG. 3 is a graph 300 showing the absorption spectra of hemoglobin, bilirubin, lipid. The graph 300 shows that at 570 nanometers and 610 nanometers, bilirubin has negligible absorption and it does not interfere. According to an aspect of the present disclosure, the close proximity of the 570 nm wavelength to the 610 nm wavelength allows for more reliable lipid correction and better chromatic image quality. It was determined that the larger hemoglobin peak at 415 nanometers is not ideal for measurement because the 415 nanometer wavelength is more susceptible to bilirubin interference and to large chromatic image degradation.

Figure 4:
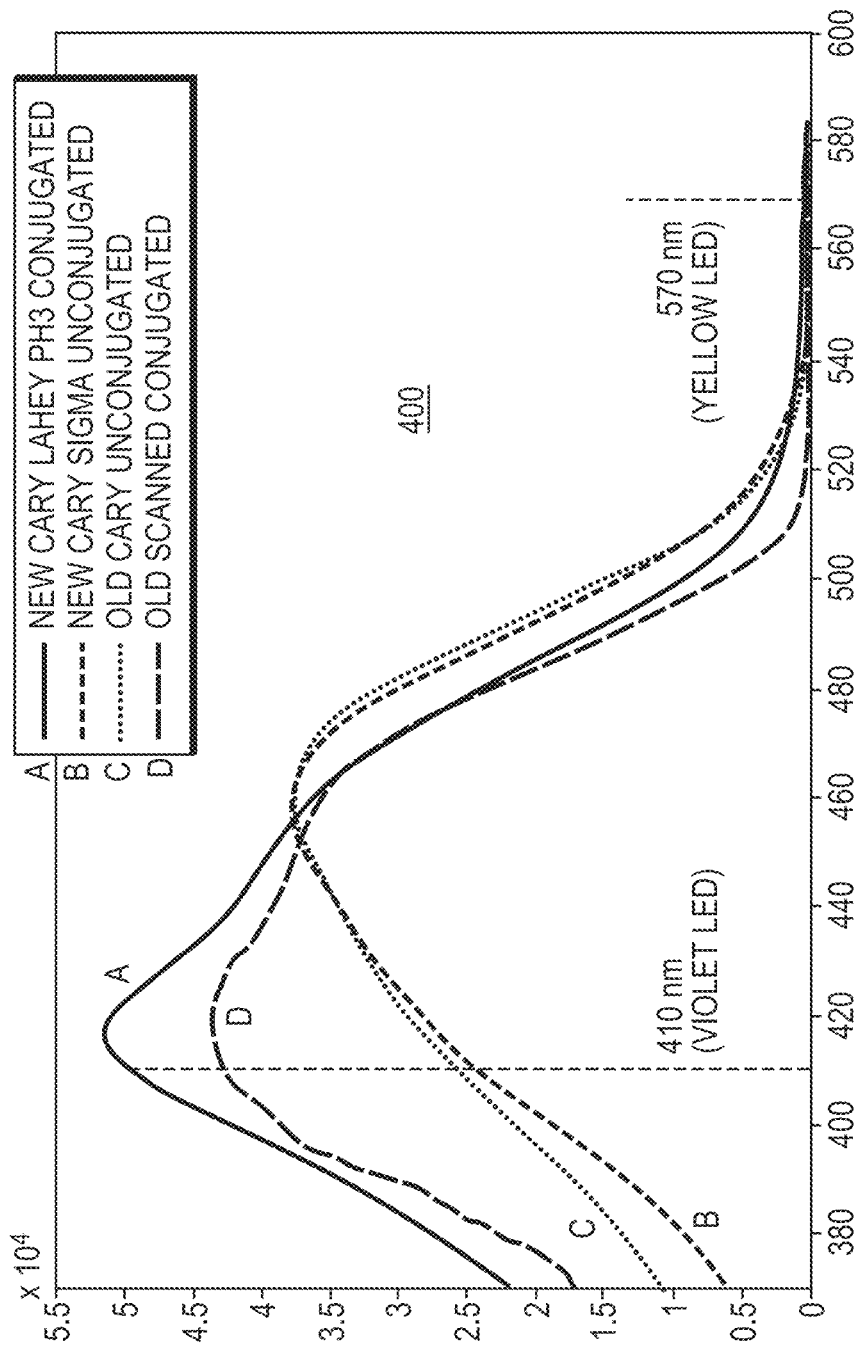
FIG. 4 is a graph showing the absorption spectra of different bilirubin species.

FIG. 4 is a graph 400 showing the absorption spectra of different bilirubin species, i.e., a conjugated bilirubin species and and unconjugated bilirubin species. The graph 400 in FIG. 4 shows that bilirubin interference at 415 nanometers is more pronounced where the spectra of two different bilirubin species are shown. The two different bilirubin species contribute different amount at 410-415 nanometers but none at 570 nanometers where no interference is shown. For at least this reason, the hemoglobin level is more complicated to measure at 410-415 nanometers than at the preferred wavelength of 570 nanometers.

Images generated by the disclosed hemolysis sensor module 100 and received as signals from the optical sensor 110 therein may be processed by processing circuitry either internal to or external from the hemolysis sensor module 100. Another aspect of the present disclosure includes two different algorithms for processing the images. The two algorithms are referred to herein as the OD algorithm and the concentration algorithm. Both of these algorithms include generating a histogram from all the pixel values received by optical sensing of the clear image plasma region. The peak of the generated histogram can then be used to calculate the hemoglobin value.

In the OD algorithm, the histogram is generated by processing OD image pixels. In the concentration algorithm, the histogram is generated by processing concentration image pixels. According to an aspect of the present disclosure, the histograms generated by processing of the concentration image pixels are more robust for determining the peak values than the histograms generated by processing OD image pixels for determining the peak values.

According to an aspect of the present disclosure illumination of the flow cell 104 with light source 108 that includes a multi-color LED is important. It is also important that illumination is as homogenized and uniform for all colors as possible. In an illustrative embodiment, these conditions can be achieved by configuring a low cost light pipe in front of the light source 108 to homogenize the two LED colors.

According to another aspect of the present disclosure, it is important to provide a very stable LED light source in the hemolysis sensor module 100. For an optical measurement error of 10 percent by the hemolysis sensor module 100 translates to about a 2 mOD absorption attenuation value or less than 0.5% noise in the yellow LED. This means that the LED output must be very stable and cannot vary by more than 0.5% in output level. However, the LED output intensity is very sensitive to temperature and can easily surpass the allowable level. Conventional methods to stabilize temperature or correct the output variations are not practical for this purpose. For example, heat sinks are too expensive, operating at lower currents is too restrictive, and adding a monitor sensor is too expensive. Also, ambient temperature inside an instrument cartridge may fluctuate and change the LED output. These changes can be the source of excessive error. According to an aspect of the present disclosure, LED output may be corrected by image processing without using extra components.

According to an aspect of the present disclosure a module for analyzing one or more plasma analytes, such as free hemoglobin, in whole blood includes a flow cell configured for housing a column of the whole blood in said module. The flow cell includes a lumen and walls surrounding the lumen.

The module includes an acoustic transducer configured for generating acoustic forces on the flow cell. The acoustic forces temporarily partition the whole blood in the flow cell into a first region comprising substantially cell free plasma clear of cellular components of said whole blood and a second region comprising blood cells. The substantially cell free plasma is localized in the lumen of the flow cell and the cellular components of the whole blood are localized at the walls of the flow cell. The flow cell also includes an inlet and an outlet for the whole blood.

The module also includes a light source configured to illuminate the substantially cell free plasma in the first region and one or more optical imaging sensors configured to acquire one or more digital images of the substantially cell free plasma in the first region while the substantially cell free plasma is illuminated by said light source. In an illustrative embodiment, the light source includes one or more LEDs. The LEDs may be multicolored LEDs which preferably emit yellow and/or red color light wherein the red color has a wavelength of about 570 nanometers and the yellow color has a wavelength of about 610 nanometers. A light pipe may be configured between the LEDs and the flow cell to facilitate homogenization of the LED colors.

In an illustrative embodiment, the imaging sensor is a camera including an image sensor board and imaging lenses. The camera includes an optical aperture installed at the imaging lenses for controlling optical aberrations. In an illustrative embodiment, the light source includes a diffuser element for uniformly illuminating the flow cell.

The module also includes a housing configured for removable installation in an instrument cartridge, wherein the housing is further configured to locate the flow cell, the light source and the optical imaging sensors in fixed alignment relative to each other. In an illustrative embodiment, the module may be configured for removable installation in one or more instruments and may be disposable. In an illustrative embodiment an electrical connector is configured to deliver electrical power and control signals to and from the module.

In an illustrative embodiment, the module also includes memory configured to store the digital images and processor circuitry in communication with the memory. The processor circuitry is configured to analyze the digital images to characterize one or more analytes in the substantially cell free plasma. For example, the processing circuitry may be configured to execute an image processing algorithm that generates a histogram of pixel values for each of the one or more digital images. In an illustrative embodiment the histogram is representative of an absorption spectra of the one or more plasma analytes. In another illustrative embodiment the histogram is representative of concentration of the one or more plasma analytes. The processing circuitry can also be configured to execute a glass correction algorithm to compensate for any fluctuations in LED intensity, for example.

The invention claimed is:

1. A sensor module for analyzing one or more plasma analytes in whole blood, comprising:
    a channel configured to house a column of the whole blood in the sensor module;
    an acoustic transducer configured to generate acoustic forces on the channel, the acoustic forces for temporarily partitioning the whole blood in the channel into a first region comprising substantially cell-free plasma that is clear of cellular components of the whole blood and a second region comprising blood cells;
    a light source configured to illuminate the substantially cell-free plasma in the first region;
    one or more optical imaging sensors configured to acquire one or more digital images of the substantially cell-free plasma in the first region while the substantially cell-free plasma is illuminated by the light source, the one or more digital images being usable for analyzing the one or more plasma analytes;
    a housing configured for removable installation of the sensor module in an instrument cartridge of an instrument configured to perform one or more analyses on a blood sample, wherein the housing is configured to locate the channel, the light source, and the one or more optical imaging sensors in fixed alignment relative to each other, and wherein the housing comprises an inlet port and an outlet port such that when the sensor module is installed in the instrument cartridge, the whole blood sample can be delivered from a blood sample container to the sensor module; and
    a connector that is configured to pass electrical power and signals to and from the sensor module.

2. The sensor nodule claim 1, further comprising:
    memory to store the one or more digital images;
    processor circuitry in communication with the memory, the processor circuitry to analyze the digital images to characterize one or more analytes in the substantially cell-free plasma.

3. The sensor module of claim 2, wherein the light source comprises one or more light emitting diodes (LEDs).

4. The sensor module of claim 3, wherein the one or more LEDs are multicolored.

5. The sensor module of claim 4, wherein the one or more LEDs are configured to emit at least one of yellow light or red light; and wherein the red light has a wavelength of about 570 nanometers and the yellow light has a wavelength of about 610 nanometers.

6. The sensor module of claim 3, further comprising:
a light pipe between the one or more LEDs and the channel, wherein the light pipe is configured to facilitate homogenization of colors of the one or more LEDs.

7. The sensor module of claim 3, wherein the processing circuitry is configured to compensate for fluctuations in LED intensity.

8. The sensor module of claim 2, wherein the processing circuitry is configured to generate a histogram of pixel values for each of the one or more digital images.

9. The sensor module of claim 8, wherein the histogram is representative of an absorption spectra of the one or more plasma analytes.

10. The sensor module of claim 8, wherein the histogram is representative of concentration of the one or more plasma analytes.

11. The sensor module of claim 1, wherein the channel comprises a hole and walls surrounding the hole.

12. The sensor module of claim 1, wherein the substantially cell-free plasma is localized in the hole of the channel and the cellular components of whole blood are localized at the walls of the channel.

13. The sensor module of claim 1, wherein the sensor module is configured for removable installation in one or more instrument cartridges.

14. The sensor module of claim 1, wherein the one or more analytes comprise free hemoglobin.

15. The sensor module of claim 1, wherein the one or more optical imaging sensors comprise a camera, the camera comprising an image sensor board and imaging lenses.

16. The sensor module of claim 15, wherein the camera comprises an optical aperture installed at the imaging lenses for controlling optical aberrations.

17. The sensor module of claim 1, wherein the light source comprises a diffuser element for uniformly illuminating the channel.

18. The sensor module of claim 1, wherein the sensor module is disposable.

19. The sensor module of claim 1, wherein signals to the sensor module comprises control signals.

20. A sensor module for analyzing one or more plasma analytes in whole blood, comprising:
a channel configured to house a column of the whole blood in the module;
an acoustic transducer configured to generate acoustic forces on the channel, the acoustic forces for temporarily partitioning the whole blood in the channel into a first region comprising substantially cell-free plasma that is clear of cellular components of the whole blood and a second region comprising blood cells;
a light source configured to illuminate the substantially cell-free plasma in the first region;
one or more optical imaging sensors configured to acquire one or more digital images of the substantially cell-free plasma in the first region while the substantially cell-free plasma is illuminated by the light source; and
a housing configured for removable installation of the sensor module in an instrument cartridge of an instrument, wherein the housing is configured to locate the channel, the light source, and the optical imaging sensors in fixed alignment relative to each other, and wherein the housing comprises an inlet port and an outlet port to enable installation of the sensor module in-line with whole blood that flows within the instrument cartridge.

* * * * *